US006060076A

United States Patent [19]
Voris et al.

[11] Patent Number: 6,060,076
[45] Date of Patent: May 9, 2000

[54] METHOD AND APPARATUS FOR PROVIDING LONG TERM PROTECTION FROM INTRUSION BY INSECTS AND OTHER COLD BLOODED ANIMALS

[75] Inventors: Peter Van Voris, Richland; Dominic A. Cataldo, Kennewick, both of Wash.

[73] Assignee: Battelle Memorial Institute, Richland, Wash.

[21] Appl. No.: 08/482,300

[22] Filed: Jun. 7, 1995

Related U.S. Application Data

[63] Continuation-in-part of application No. 08/348,774, Dec. 1, 1994, abandoned, which is a continuation of application No. 08/117,877, Sep. 7, 1993, abandoned, which is a continuation of application No. 07/893,970, Jun. 4, 1992, abandoned, which is a continuation of application No. 07/401,955, Sep. 1, 1989, abandoned, which is a continuation-in-part of application No. 06/555,113, Nov. 23, 1983, Pat. No. 5,116,414, which is a continuation-in-part of application No. 06/314,809, Oct. 26, 1981, abandoned, which is a continuation-in-part of application No. 06/314,810, Oct. 26, 1981, abandoned.

[51] Int. Cl.⁷ .......................... A01N 25/10; A01N 25/34; A01N 37/12; A01N 47/40
[52] U.S. Cl. .......................... 424/411; 514/521; 514/531; 514/772.3; 514/953
[58] Field of Search .......................... 514/59, 521, 531, 514/723.3, 953; 71/DIG. 1; 504/116; 424/411

[56] References Cited

U.S. PATENT DOCUMENTS

| | | | |
|---|---|---|---|
| Re. 32,356 | 2/1987 | Cardarelli | 424/78 |
| 1,999,458 | 4/1935 | Hollister | 47/1 |
| 2,970,404 | 2/1961 | Beaufils et al. | 47/57.5 |

(List continued on next page.)

FOREIGN PATENT DOCUMENTS

| | | |
|---|---|---|
| 23427/84 | 8/1984 | Australia . |
| 48655/90 | 8/1990 | Australia . |
| 62329/90 | 6/1991 | Australia . |
| 91/82443 | 8/1991 | Australia . |
| B-82443/91 | 2/1992 | Australia ...... A01N 25/10 |
| 95/13886 A1 | 8/1995 | Australia . |
| 52454/96 | 12/1996 | Australia . |
| 2 070 231 | 12/1992 | Canada . |
| 0 286 009 A2 | 10/1988 | European Pat. Off. ......... B27K 3/50 |
| 0 594 892 | 5/1994 | European Pat. Off. . |
| 52-72802 | 6/1977 | Japan ............... B27K 3/34 |
| 58-39601 | 3/1983 | Japan . |
| 86/1133 | 2/1986 | South Africa . |
| 2 018 593 | 10/1979 | United Kingdom . |
| 2 098 541 | 11/1982 | United Kingdom . |
| WO 84/02447 | 7/1984 | WIPO ............ A01N 25/34 |
| WO90/14004 | 11/1990 | WIPO . |
| WO 95/18532 | 7/1995 | WIPO ............ A01N 25/34 |
| WO97/47190 | 12/1997 | WIPO . |

OTHER PUBLICATIONS

Batelle Technology Transfer Bulletin, "Controlled–Release Chemicals for Inhibiting Plant Roots," 2 pgs. (Dec. 1984).
Cline et al., "Biobarriers used in Shallow Burial Ground Stabilization," *Nuclear Technology*, vol. 58, pp. 150–153 (1982).
Hughes, "Controlled Release Technology Inhibits Root Growth," *Controlled Release*, p. 15. no date.
Jury et al., "Behaviour Assessment Model for Trace Organics in Soil: I. Model Description," *J. Environ. Qual.*, vol. 12, No. 4, pp. 558–564 (1983).
Jury et al., "Behaviour Assessment Model for Trace Organics in Soil: III. Application of Screening Model," *J. Environ. Qual.*, vol. 13, No. 4, pp. 573–579 (1984).
Jury et al., "Behaviour Assessment Model for Trace Organics in Soil: IV. Review of Experimental Evidence," *J. Environ. Qual.*, vol. 13, No. 4 (1984).
Roseman et al., "Chapter 18: The Use of Controlled Release Herbicides in Waste Burial Sites," *Controlled Release Delivery Systems* Marcel Dekker, NY (1983).
"Soil Fumigants are Remarkably Effective in Stopping Decay of Wood," *Chemical Week*, p. 39, (Sep. 25, 1974). *Abstract.
Solie et al., "Simulation of Trifluralin Diffusion in the Soil," *Transactions of the ASAE*, pp. 1463–1467 (1984).
Steyaart, "Proceedings, Eighty–Second Annual Meeting of the American Wood–Preservers' Association: Address," *Crossties*, vol. 68, No. 3, pp. 45–46 (1987).
Streile, "The Effect of Temperature on Pesticide Phase Partitioning, Trasnport, and Volatilization from Soil," *Abstract of the Dissertation*, (1984), 37 pages.
Van Voris et al., "Long–Term Controlled Release of Herbicides: Root–Growth–Inhibiting Biobarrier Technology," 19 pages.
Burton, et al., "A Controlled–ReleaseHerbicide Device for Multiple–Year Control of Roots at Waste Burial Sites," *J. of Controlled Release* (1985), 8 pages.
Chang, et al., "Control of Ant Damage to Polyethylene Tubes Used in Drip Irrigation Systems in Hawaiian Sugarcane Fields," *International Society of Sugar Cane Technologists* (Feb. 1–Nov. 1980), pp. 1686–1692.
Chen, et al., "Approaches to the Improvement of Biological Resistance of Wood through Controlled Release Technology," *Proceedings of the 13th Int'l Symposium on Controlled Release of Bioactive Materials* (Aug. 3–Jun. 1986), pp. 75–76.

*Primary Examiner*—S. Mark Clardy
*Attorney, Agent, or Firm*—Arnold White & Durkee

[57] ABSTRACT

Controlled release devices are shaped and placed in locations through which insects and/or other cold blooded animals generally enter an area or a structure sought to be protected. The controlled release devices include a polymeric matrix and a pesticide contained in the matrix. The pesticide is gradually released out of the matrix to the surface of the device. The pesticide on the surface of the device kills the intruding insects or other cold blooded animals that come in contact with the pesticide. In addition, if the device is in contact with a permeable structure or object, the pesticide released onto the surface of the device is absorbed by such permeable structure or object to provide a barrier to entry by the insects and/or other cold blooded animals.

30 Claims, No Drawings

U.S. PATENT DOCUMENTS

| | | | |
|---|---|---|---|
| 3,111,403 | 11/1963 | Soper | 71/2.3 |
| 3,257,190 | 6/1966 | Soper | 71/2.3 |
| 3,367,065 | 2/1968 | Cravens | 47/57.5 |
| 3,502,458 | 3/1970 | Schenk | 71/64 |
| 3,592,792 | 7/1971 | Newland et al. | 260/41 |
| 3,608,062 | 9/1971 | Alfes et al. | 424/22 |
| 3,639,583 | 2/1972 | Cardarelli et al. | 424/125 |
| 3,671,548 | 6/1972 | Itaya et al. | 549/79 |
| 3,691,683 | 9/1972 | Sterzik | 47/57.5 |
| 3,705,938 | 12/1972 | Hyman et al. | 424/19 |
| 3,706,161 | 12/1972 | Jenson | 47/57.5 |
| 3,716,560 | 2/1973 | Taya et al. | 549/471 |
| 3,759,941 | 9/1973 | Sampei et al. | 549/117 |
| 3,835,176 | 9/1974 | Matsuo et al. | 558/407 |
| 3,835,220 | 9/1974 | Matsui et al. | 424/40 |
| 3,846,500 | 11/1974 | Kitamura et al. | 568/660 |
| 3,851,053 | 11/1974 | Cardarelli | 424/78 |
| 3,857,934 | 12/1974 | Bernstein et al. | 424/30 |
| 3,864,114 | 2/1975 | Green | 71/3 |
| 3,864,388 | 2/1975 | Kitamura et al. | 560/60 |
| 3,867,542 | 2/1975 | Ueda et al. | 514/461 |
| 3,876,681 | 4/1975 | Okuno et al. | 560/124 |
| 3,880,643 | 4/1975 | Cooke et al. | 71/78 |
| 3,891,423 | 6/1975 | Stanley et al. | 71/86 |
| 3,899,586 | 8/1975 | Okuno et al. | 514/417 |
| 3,906,089 | 9/1975 | Okuno et al. | 424/45 |
| 3,954,814 | 5/1976 | Mizutani et al. | 549/449 |
| 3,966,963 | 6/1976 | Okuno et al. | 514/531 |
| 3,970,703 | 7/1976 | Kitamura et al. | 568/662 |
| 3,981,903 | 9/1976 | Hirano et al. | 560/124 |
| 3,998,868 | 12/1976 | Mitzutani et al. | 560/124 |
| 5,019,998 | 5/1991 | Cowen et al. | 364/496 |
| 5,104,659 | 4/1992 | Fishbein et al. | 424/411 |
| 5,116,414 | 5/1992 | Burton et al. | 71/121 |
| 5,135,744 | 8/1992 | Alexander et al. | 424/409 |
| 5,139,566 | 8/1992 | Zimmerman | 71/121 |
| 5,181,952 | 1/1993 | Burton et al. | 504/347 |
| 5,201,925 | 4/1993 | Itzel et al. | 47/58 |
| 5,292,504 | 3/1994 | Cardin et al. | 514/65 |
| 5,296,227 | 3/1994 | Norval et al. | 424/411 |
| 5,317,834 | 6/1994 | Anderson | 47/48.5 |
| 5,439,924 | 8/1995 | Mills | 514/345 |
| 5,449,250 | 9/1995 | Burton et al. | 405/128 |
| 5,492,696 | 2/1996 | Price et al. | 424/417 |
| 4,003,945 | 1/1977 | Kitamura et al. | 560/124 |
| 4,007,258 | 2/1977 | Cohen et al. | 424/22 |
| 4,021,122 | 5/1977 | Krenmayr | 356/240 |
| 4,037,352 | 7/1977 | Hennart et al. | 43/129 |
| 4,063,919 | 12/1977 | Grano, Jr. | 71/11 |
| 4,065,555 | 12/1977 | Potter | 424/83 |
| 4,077,795 | 3/1978 | Cooke et al. | 71/78 |
| 4,082,533 | 4/1978 | Wittenbrook et al. | 71/28 |
| 4,102,991 | 7/1978 | Kydonieus | 424/27 |
| 4,104,374 | 8/1978 | Reuther et al. | 424/185 |
| 4,118,505 | 10/1978 | Kitamura et al. | 514/438 |
| 4,123,250 | 10/1978 | Kupelian | 71/78 |
| 4,160,335 | 7/1979 | Von Kohorn et al. | 43/131 |
| 4,172,904 | 10/1979 | Young et al. | 427/4 |
| 4,176,189 | 11/1979 | Itaya et al. | 514/389 |
| 4,190,680 | 2/1980 | Young et al. | 427/4 |
| 4,193,984 | 3/1980 | Kydonieus | 424/16 |
| 4,198,441 | 4/1980 | Young et al. | 427/2 |
| 4,198,782 | 4/1980 | Kydonieus et al. | 47/58 |
| 4,200,664 | 4/1980 | Young et al. | 427/4 |
| 4,205,096 | 5/1980 | Young et al. | 427/4 |
| 4,212,879 | 7/1980 | Ohsumi et al. | 514/427 |
| 4,229,469 | 10/1980 | Mizutani et al. | 514/519 |
| 4,235,872 | 11/1980 | Tocker | 424/19 |
| 4,237,113 | 12/1980 | Cardarelli | 424/78 |
| 4,237,114 | 12/1980 | Cardarelli | 424/78 |
| 4,260,626 | 4/1981 | Carr et al. | 424/273 R |
| 4,263,463 | 4/1981 | Kitamura et al. | 568/873 |
| 4,269,626 | 5/1981 | Gorke et al. | 106/18.32 |
| 4,272,520 | 6/1981 | Kydonieus et al. | 424/84 |
| 4,279,924 | 7/1981 | Suzuki et al. | 514/521 |
| 4,282,207 | 8/1981 | Young et al. | 424/78 |
| 4,282,209 | 8/1981 | Tocker | 424/81 |
| 4,293,504 | 10/1981 | Suzuki et al. | 558/354 |
| 4,320,113 | 3/1982 | Kydonieus | 424/27 |
| 4,327,109 | 4/1982 | Mizutani et al. | 514/443 |
| 4,336,194 | 6/1982 | Ohsumi et al. | 548/562 |
| 4,344,250 | 8/1982 | Fahlstrom | 47/57.5 |
| 4,348,218 | 9/1982 | Bond, Jr. | 71/1 |
| 4,350,678 | 9/1982 | Palvarini et al. | 424/27 |
| 4,352,833 | 10/1982 | Young et al. | 427/4 |
| 4,360,376 | 11/1982 | Koestler | 71/121 |
| 4,374,126 | 2/1983 | Cardarelli et al. | 424/81 |
| 4,376,785 | 3/1983 | Matsuo et al. | 514/521 |
| 4,377,675 | 3/1983 | Daudt et al. | 528/25 |
| 4,400,374 | 8/1983 | Cardarelli | 424/78 |
| 4,405,360 | 9/1983 | Cardarelli | 71/117 |
| 4,435,383 | 3/1984 | Wysong | 424/78 |
| 4,457,929 | 7/1984 | Kamachi et al. | 424/246 |
| 4,496,586 | 1/1985 | Matsui et al. | 514/531 |
| 4,500,337 | 2/1985 | Young et al. | 71/67 |
| 4,500,338 | 2/1985 | Young et al. | 71/67 |
| 4,500,339 | 2/1985 | Young et al. | 71/67 |
| 4,503,071 | 3/1985 | Hirano et al. | 514/521 |
| 4,508,568 | 4/1985 | Fox | 106/2 |
| 4,576,605 | 3/1986 | Parry et al. | 427/288 |
| 4,579,085 | 4/1986 | McGuire | 119/156 |
| 4,639,393 | 1/1987 | Von Kohorn et al. | 428/304.4 |
| 4,666,706 | 5/1987 | Farquharson et al. | 424/408 |
| 4,666,767 | 5/1987 | Von Kohorn et al. | 428/304.4 |
| 4,680,328 | 7/1987 | Dohrer et al. | 524/137 |
| 4,747,902 | 5/1988 | Saitoh | 156/244.11 |
| 4,767,812 | 8/1988 | Chapin et al. | 524/144 |
| 4,808,454 | 2/1989 | Saitoh | 428/40.6 |
| 4,818,525 | 4/1989 | Kamada et al. | 424/81 |
| 4,842,860 | 6/1989 | Suguira et al. | 424/403 |
| 4,886,656 | 12/1989 | Obayashi et al. | 514/144 |
| 4,921,703 | 5/1990 | Higuchi et al. | 424/419 |
| 4,929,497 | 5/1990 | Mitchell et al. | 428/265 |

METHOD AND APPARATUS FOR PROVIDING LONG TERM PROTECTION FROM INTRUSION BY INSECTS AND OTHER COLD BLOODED ANIMALS

CROSS REFERENCE TO RELATED APPLICATIONS

The present application is a Continuation-in-Part of U.S. patent application Ser. No. 08/348,774, abandoned, filed on Dec. 1, 1994, which is a continuation of U.S. patent application Ser. No. 08/117,877, abandoned, filed on Sep. 7, 1993, which is a continuation of U.S. patent application Ser. No. 07/893,970, abandoned, filed on Jun. 4, 1992, which is a continuation of U.S. patent application Ser. No. 07/401,955, abandoned, filed on Sep. 1, 1989, which is a continuation-in-part of U.S. patent application Ser. No. 06/555,113, now U.S. Pat. No. 5,116,414, filed on Nov. 23, 1983, which is a continuation-in-part of U.S. patent application Ser. Nos. 06/314,809 and 06/314,810, both filed on Oct. 26, 1981 and now abandoned.

BACKGROUND OF THE INVENTION

This invention relates to methods and devices for preventing insects and other cold blooded animals from intruding into certain areas or certain structures. In particular, it relates to providing long term protection against such intrusions.

Insects and other cold blooded animals need to be kept out certain areas and/or certain structures. Their intrusions into such areas or structures can create problems ranging in severity from merely a nuisance to those having dire consequences. For example, fire ants have to be kept out of electrical power distribution enclosures. Their intrusion into such enclosures can cause damage or even destruction of the electrical power distribution system. Fire ants also create a nuisance or damage by entering into buildings through cracks in the walls. In addition, the existence of fire ants in a quarantine zone can cause considerable expense to the plant nurseries in such zone. The plants which are shipped outside the zone must be certified to be ant free. The procedures used to assure that potted plants do not contain fire ants are relatively expensive and time consuming.

Similarly, intrusions by spiders of houses often produce unsightly webs which may be difficult to reach and eliminate.

In some areas, cold blooded animal other than insects create problems. For example, the brown tree snake, a venomous constrictor is a problem in the Pacific Islands, such as Guam and Hawaii where they frequently invade homes in search of food. Their control has been limited because of the collateral impact any effective control, would have on the endangered species.

Finally, crawling insects and soil borne insects can destroy crops and can create a nuisance and damage living areas.

SUMMARY OF THE INVENTION

Controlled release devices are shaped and placed in locations through which insects and/or other cold blooded animals generally enter an area or a structure sought to be protected. For the devices to be effective the release rate of the pesticide must be at least 10 $\mu g/cm^2/day$ for insects and must be at least 40 $\mu g/cm^2/day$ for cold blooded vertebrae animals. The controlled release devices include a polymeric matrix and a pesticide contained in the matrix. The pesticide is gradually released out of the matrix to the surface of the device. The pesticide on the surface of the device kills the intruding insects or other cold blooded animals that come into contact with the pesticide. In addition, if the device is in contact with a permeable structure or object, the pesticide released onto the surface of the device is absorbed by such permeable structure or object to provide a barrier to entry by the insects and/or other cold blooded animals. The pesticides that have been found useful in connection with the present invention include pyrethrins and fenoxycarb. The polymeric matrices can be made from any polymer which provides desired release rates and incorporates the pesticide without effecting its pesticidal activity. The preferred polymers include silicones, EVA, urethanes, polyurethanes, acrylonitrile butadene, acrylic rubber, isoprene and styrene-vinyl rubber.

The present invention is particularly useful in preventing intrusions by fire ants, spiders, crawling insects and other cold blooded animals such as snakes and lizards.

DETAILED DESCRIPTION

It has been discovered that controlled release devices which gradually release pesticides can be constructed to prevent, for a prolonged period of time, intrusions by insects and/or other cold blooded animals into areas, structures or objects that are sought to be protected from intrusions. The protection offered by the controlled release devices constructed and used in accordance with the present invention generally lasts from about 6 months to about 5 years.

Any polymer which can provide the desired release rate and which does not destroy the pesticidal nature of the pesticide used in the device can be employed to provide a polymeric in accordance with the present invention. Generally, suitable polymers can include both thermoset and thermoplastic polymers. Currently preferred polymers are silicones, urethanes, polyurethanes, acrylonitrile butadiene, acrylic rubber, styrene-vinyl rubber EVA and polyethylenes. Especially preferred are the following polymers: RTV-41, Hytrel, Solithane, Nipol 1312, Nipol 1312 LV, Hycar X16, Kraton D1101, Ultra Clear, Aromatic 80A urethane, Pellethane 2102-80A, Pellethane 2102-55D Alipmtic PS-49-100, Polyurethane 3100, Polyurethane 2200, EVA 763, Polyethylene MA 7800, and Polyethylene MA 78000.

Pesticides that can be employed in the matrices of the present invention include those that provide desired release rates at least about 10 $\mu g/cm^2/day$ for insects and at least about 40 $\mu g/cm2/day$ for cold blooded vertebras can be incorporated into a polymeric matrix and whose matricidal quality is not destroyed by incorporation in the matrix. The concentration of the pesticide in the matrix is generally in the range from about 2 to about 15 percent of the total weight of he matrix and preferably in the range from about 5 to about 10 percent.

In some control release devices of the present invention a carrier can be included to produce a desired release rate. A carrier can be carbon black clay or amorphous silica. Carbon black is currently preferred. The concentration of the carrier can range from about 2 to about 5 percent per total weight of the matrix, preferably it is in the range from about 3 to about 5 percent.

A description of general principles of making controlled release devices is given in U.S. patent application Ser. No. 06/555,113 filed Nov. 23, 1983 which is a continuation in part of Ser. Nos. 06/314,809 and 06/314,810 both filed on Oct. 26, 1981; Ser. No. 07/086,757, filed Aug. 18, 1987, Ser. No. 07/072,080 filed Jul. 10, 1987; and Ser. No. 07/091,918 filed Sep. 1, 1987. Methods for obtaining the release rates are described in patent application Ser. No. 07/303,707 filed on Jan. 30, 1989. The contents of these applications are being incorporated herein by reference.

Specifically the following passages from these applications relate to general principles of making controlled release devices:

page 14, line 12—page 26, line 11 of Ser. No. 06/555,113;

page 4, line 5 starting with "Carbon"—page 5, line 3 of Ser. No. 07/086,757;

page 4, line 15—page 6, line 2 of Ser. No. 06/314,809; and page 6, line 4—page 9, line 13 of Ser. No. 06/314,809;

page 3, line 33—page 6, line 26 of Ser. No. 06/314,810;

page 6, lines 15–17 of Ser. No. 07/072,080;

page 3, line 22—page 4, line 20 of Ser. No. 07/91,918;

page 2, line 21–26 and page 2, line 34—page 6, line 8 and page 15, line 25—page 17, line 17 of Ser. No. 07/303,707.

The protection against intrusion is provided by the present invention as the result of the accumulation of the pesticide on the surface of the polymer matrix and/or the accumulation of the pesticide in an absorbent medium in contact with or in close proximity to the matrix, when the insect or other cold blooded animal comes in contact with pesticide it is repelled by it and/or killed by it. In case of insects, the pesticide is generally transferred to the feet of the insects and when the release rate of the pesticide is at least about 10 $\mu g/cm2/day$, sufficient amount of pesticide adheres to insect to kill it. It has been discovered that faster release rates are necessary for larger cold blooded animals. For snakes, and other cold blooded vertebrae animals, the pesticide release rates must be at least 40 $\mu g/cm2/day$.

EXAMPLE

The following controlled release devices were made and tested to obtain their release rates. The devices were made as follows. All devices, except for those employing S-113 urethane, were injection molded into a thin sheet about ⅛ inch thick. The device employing S-113 urethane was cast, a method typically used for thermoset polymers. All thermoplastics were formulated using sufficient amount of carbon black to carry pesticides. All thermoplastic polymers were formulated with 10 percent pesticide, 3 or 7 percent carbon black to absorb liquid pesticide and 87 to 83 percent by weight of polymer. Specifically, devices made from thermoplastic polymers and deltamethrin and lambdacyhalothrin contained 3 percent of carbon black. The devices made from the remaining pesticides and thermoplastic polymers contained 7 percent of carbon black.

The devices made from S-113 urethane (a thermoset polymer) were made from a polymer mix containing 60% S-113, 40% castor oil and 5% of TIPA catalyst by weight. The polymer mix comprised 90% of the total weight of the device. The pesticide, deltamethrin, comprised the remaining 10% of the device. No carbon black was used in this device. The polymer/pesticide mixture was cast, using a spin caster into a ⅛ inch thick sheet and heated at about 60° C. for about 40 to 60 minutes to cure the cast sheet.

On inch squares were then cut from the thin sheets that were injection molded or cast and the squares were tested for release rates. The following release rates were obtained:

| Pesticide | Polymer | Release Rate |
|---|---|---|
| Deltamethrin | S-113 urethane | 25.2 $\mu g/cm2/day$ |
|  | Aromatic 80A | 16.8 $\mu g/cm2/day$ |
|  | pellethane 2102-80A | 8.8 $\mu g/cm2/day$ |
|  | pellethane 2102-55D | 8.0 $\mu g/cm2/day$ |
|  | Alipmtic PS-49-100 | 7.2 $\mu g/cm2/day$ |
| Cypermethrin | polyurethane 3100 | 0.4 $\mu g/cm2/day$ |
|  | polyurethane 2200 | 0.7 $\mu g/cm2/day$ |
|  | EVA 763 | 27.3 $\mu g/cm2/day$ |
|  | Polyethylene MA7800 | 4.6 $\mu g/cm2/day$ |
| Lambdacyhalothrin | polyurethane 3100 | 0.7 $\mu g/cm2/day$ |
|  | polyurethane 2200 | 2.0 $\mu g/cm2/day$ |
|  | EVA 763 | 20.6 $\mu g/cm2/day$ |
|  | Polyethylene MA78000 | 5.2 $\mu g/cm2/day$ |
| Tefluthrin | polyurethane 3100 | 6.4 $\mu g/cm2/day$ |
|  | polyurethane 2200 | 25.0 $\mu g/cm2/day$ |
|  | EVA 763 | 40.4 $\mu g/cm2/day$ |
|  | Polyethylene MA78000 | 27.0 $\mu g/cm2/day$ |
| Permethrin | polyurethane 3100 | 1.4 $\mu g/cm2/day$ |
|  | polyurethane 2200 | 1.3 $\mu g/cm2/day$ |
|  | EVA 763 | 28.5 $\mu g/cm2/day$ |
|  | Polyethylene MA78000 | 4.0 $\mu g/cm2/day$ |

From the foregoing description one skilled in the art can easily ascertain the essential characteristics of this invention and without department from the spirit and scope of the invention thereof can make changes and modifications of the invention in order to adapt it to the various usages and conditions. It is intended that the scope of the invention be defined by the following claims including all equivalents.

We claim:

1. A method for creating a barrier to entry of crawling or soil borne insects to provide long-term protection of an area or a structure from intrusion by said insects, said method comprising the following steps:

(a) placing a controlled release barrier at the entry points to said area or said structure, said barrier having an outside surface and comprising a polymeric matrix and a pesticide within said matrix;

(b) allowing the pesticide to release onto the outside surface of the controlled release barrier and accumulate on said outside surface, the release rate of the pesticide being at least 10 $\mu g/cm^2/day$, said rate being sufficient to repel or kill insects coming in contact with the surface of the barrier so as to protect said area or said structure from intrusion by said crawling or soil borne insects.

2. A method for creating a barrier to entry of crawling or soil borne insects to provide long-term protection of an area or a structure from intrusion by cold-blooded vertebrae animals, said method comprising the following steps:

(a) placing a controlled release barrier at the entry points to said area of structure, said barrier having an outside surface;

(b) allowing the pesticide to release onto the outside surface of the controlled release barrier and accumulate on said outside surface, the release rate of the pesticide being at least 40 $\mu g/cm2/day$, said rate being sufficient to repel or kill animals coming in contact with the surface of the barrier so as to protect said area or said structure from intrusion by said cold-blooded vertebrae animals.

3. The method of claim 1 wherein the polymeric matrix is selected from a group consisting of silicones, EVA, urethanes, polyurethanes, acrylonitrile, butadene, acrylic rubber, isoprene and styrene-vinyl rubber.

4. The method of claim 3 wherein the polymeric matrix further includes a carrier for controlling the release rate.

5. The method of claim 4 wherein the carrier is selected from the group consisting of carbon black, clay or amorphous silica.

6. The method of claim 5 wherein the carrier is carbon black.

7. The method of claim 3 wherein the concentration of the carrier is from about 2 to about 7 percent per total weight of the matrix.

8. The method of claim 5 wherein the concentration of the carrier is from about 3 to about 5 percent per total weight of the matrix.

9. The method of claim 1 wherein the concentration of the pesticide is in the range from about 2 to about 15 percent of the total weight of the matrix.

10. The method of claim 4 wherein the concentration of pesticide is from about 5 to about 10 percent of the total weight of the matrix.

11. The method of claim 9 wherein the pesticide is deltamethrin.

12. The method of claim 9 wherein the pesticide is cypermethrin.

13. The method of claim 9 wherein the pesticide is lamdacyhalothrin.

14. The method of claim 9 wherein the pesticide is tefluthrin.

15. The method of claim 9 wherein the pesticide is permethrin.

16. The method of claim 1 wherein the device is large enough to continue releasing the pesticide at a rate above 10 $\mu g/cm^2/day$ for a time period from about 6 months to 5 years.

17. The method of claim 1 wherein the polymeric matrix is selected from a group consisting of silicones, EVA, urethanes, polyurethanes, acrylonitrile, butadene, acrylic rubber, isoprene and styrene-vinyl rubber.

18. The method of claim 17 wherein the polymeric matrix further includes a carrier for controlling the release rate.

19. The method of claim 18 wherein the carrier is selected from the group consisting of carbon black, clay or amorphous silica.

20. The method of claim 19 wherein the carrier is carbon black.

21. The method of claim 17 wherein the concentration of the carrier is from about 2 to about 7 percent of the total weight of the device.

22. The method of claim 19 wherein the concentration of the carrier is from about 3 to about 5 percent of the total weight of the device.

23. The method of claim 1 wherein the concentration of the pesticide is in the range from about 2 to about 15 percent of the total weight of the device.

24. The method of claim 18 wherein the concentration of pesticide is from about 5 to about 10 percent of the total weight of the device.

25. The method of claim 23 wherein the pesticide is deltamethrin.

26. The method of claim 23 wherein the pesticide is cypermethrin.

27. The method of claim 23 wherein the pesticide is lamdacyhalothrin.

28. The method of claim 23 wherein the pesticide is tefluthrin.

29. The method of claim 23 wherein the pesticide is permethrin.

30. The method of claim 23 wherein the device is large enough to continue releasing the pesticide at a rate above 10 $\mu g/cm^2/day$ for a time period from about 6 months to 5 years.

* * * * *

UNITED STATES PATENT AND TRADEMARK OFFICE
CERTIFICATE OF CORRECTION

PATENT NO. : 6,060,076 Page 1 of 1
APPLICATION NO. : 08/482300
DATED : May 9, 2000
INVENTOR(S) : Voris et al.

It is certified that error appears in the above-identified patent and that said Letters Patent is hereby corrected as shown below:

On the title page

Item 75 please add --Crystal J. Driver--

Signed and Sealed this

Third Day of October, 2006

JON W. DUDAS
*Director of the United States Patent and Trademark Office*